US009498748B2

(12) United States Patent
Wagner et al.

(10) Patent No.: US 9,498,748 B2
(45) Date of Patent: Nov. 22, 2016

(54) REMOVAL OF ACID GASES FROM A FLUID FLOW BY MEANS OF REDUCED COABSORPTION OF HYDROCARBONS AND OXYGEN

(71) Applicant: BASF SE, Ludwigshafen (DE)

(72) Inventors: Rupert Wagner, Worms (DE); Ute Lichtfers, Karlsruhe (DE); Norbert Asprion, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/782,316

(22) Filed: Mar. 1, 2013

(65) Prior Publication Data

US 2013/0175471 A1    Jul. 11, 2013

Related U.S. Application Data

(62) Division of application No. 12/301,408, filed as application No. PCT/EP2007/054716 on May 15, 2007, now abandoned.

(30) Foreign Application Priority Data

May 18, 2006    (EP) .................... 06114184

(51) Int. Cl.
  *B01D 53/14*    (2006.01)
  *B01D 53/40*    (2006.01)
  *C07C 7/11*    (2006.01)

(52) U.S. Cl.
  CPC ....... *B01D 53/1493* (2013.01); *B01D 53/1456* (2013.01); *C07C 7/11* (2013.01)

(58) Field of Classification Search
  USPC ...... 423/220, 228, 235, 240 R, 242.1, 242.3, 423/242.7; 562/553, 575; 564/503, 506
  See application file for complete search history.

(56) References Cited

U.S. PATENT DOCUMENTS

| 3,042,483 | A | * | 7/1962 | Wolfram | ................ B01D 47/00 423/437.1 |
| 4,035,166 | A | * | 7/1977 | Van Hecke | ........ B01D 53/1456 423/232 |

(Continued)

FOREIGN PATENT DOCUMENTS

| CA | 2642328 A1 | 12/2004 |
| EP | 0125358 A1 | 11/1984 |

(Continued)

OTHER PUBLICATIONS

"Gaseous Fuels and Chemical Consumption." The Engineering ToolBox (no publishing date). Viewed on Apr. 24, 2014 at http://www.engineeringtoolbox.com/chemical-composition-gaseous-fuels-d_1142.html.*

(Continued)

*Primary Examiner* — Stuart Hendrickson
*Assistant Examiner* — Daniel Berns
(74) *Attorney, Agent, or Firm* — Drinker Biddle & Reath LLP

(57) ABSTRACT

A process for removing acid gases from a hydrocarbonaceous fluid stream or an oxygen-comprising fluid stream in which the fluid stream is contacted with an aqueous solution which is essentially free from inorganic basic salts and comprises (i) at least one amine and (ii) at least one metal salt of an aminocarboxylic acid and/or an aminosulfonic acid. Conjoint use of the aminocarboxylic and/or aminosulfonic salt reduces the coabsorption of hydrocarbons or oxygen without significantly impairing the absorption rate at which acid gases are absorbed, without significantly reducing the absorption capacity of the solution for acid gases, and without significantly increasing the energy demand required for regeneration.

12 Claims, 3 Drawing Sheets

(56) References Cited

U.S. PATENT DOCUMENTS

| | | | |
|---|---|---|---|
| 4,094,957 | A | 6/1978 | Sartori et al. |
| 4,278,646 | A | 7/1981 | Lynn et al. |
| 4,336,233 | A | 6/1982 | Appl et al. |
| 6,500,397 | B1 | 12/2002 | Yoshida et al. |
| 2009/0320682 | A1 | 12/2009 | Wagner et al. |
| 2012/0051989 | A1 | 3/2012 | Wagner et al. |

FOREIGN PATENT DOCUMENTS

| | | |
|---|---|---|
| EP | 0671200 | 9/1995 |
| GB | 1543748 A | 4/1979 |

OTHER PUBLICATIONS

Canadian Office Action dated Feb. 24, 2014 in reference to co-pending CA patent application 2,651,896.

\* cited by examiner

REMOVAL OF ACID GASES FROM A FLUID FLOW BY MEANS OF REDUCED COABSORPTION OF HYDROCARBONS AND OXYGEN

CROSS-REFERENCE TO RELATED APPLICATIONS

This Application is a Division of application Ser. No. 12/301,408 filed on Nov. 18, 2008, the entire contents of which are incorporated herein by reference. Application Ser. No. 12/301,408 is a national stage application, under 35 U.S.C. §371, of PCT/EP2007/054716, filed May 15, 2007, the entire contents of which are incorporated herein by reference, which claims priority to European Application No. 06114184.2, filed May 18, 2006, the entire contents of which are incorporated herein by reference.

The present invention relates to a process for removing acid gases from a fluid stream, and to an absorption medium.

The removal of acid gases such as, for example, $CO_2$, $H_2S$, $CS_2$, HCN, COS or mercaptans, from fluid streams, such as natural gas, refinery gas, synthesis gas, is of importance for differing reasons. The sulfur compound content of natural gas must be reduced by suitable treatment measures directly at the natural gas well, since the sulfur compounds form acids in the water frequently entrained by the natural gas, which acids are corrosive. To transport the natural gas in a pipeline, therefore, preset limiting values of the sulfurous impurities must be met. Reduction of the carbon dioxide content is frequently required to establish a preset calorific value.

The removal of carbon dioxide from exhaust gases is desirable for various reasons, but in particular for reducing carbon dioxide emissions which are regarded as the main cause of what is known as the greenhouse effect.

To remove acid gases, use is made of scrubbing stages with aqueous solutions of inorganic or organic bases. On dissolution of acid gases in the absorption medium, ions form with the bases. The absorption medium can be regenerated by expansion to a lower pressure and/or stripping, the ionic species back-reacting to form acid gases and/or being stripped off by a means of steam. After the regeneration process, the absorption medium can be reused. Absorption medium described in U.S. Pat. No. 4,336,233 is also particularly proven. This is an aqueous solution of methyldiethanolamine (MDEA) and piperazine as absorption accelerator or activator. The scrubbing liquid described comprises 1.5 to 4.5 mol/l of methyldiethanolamine (MDEA) and 0.05 to 0.8 mol/l, preferably up to 0.4 mol/l, of piperazine.

Although hydrocarbons are per se water insoluble, owing to the high content of organic amines, the aqueous amine solutions which are used for removing acid gases have a not insignificant lipophilic character. This leads to coabsorption of hydrocarbons when hydrocarbonaceous fluids are treated with the aqueous amine solution. Hydrocarbon coabsorption is disadvantageous for many reasons. Hydrocarbons are the primary product of value of many fluid streams. Hydrocarbon coabsorption therefore leads to an unwanted loss of product of value. Although the absorbed hydrocarbons can be liberated from the loaded absorption medium in an upstream expansion stage before the absorption medium is regenerated and freed from the acid gases, this necessitates an additional process expenditure. In many cases the purity of the acid gas produced is also relevant. For example the hydrogen sulfide separated off can be passed to a sulfur recovery unit (SRU) in which it is catalytically oxidized to sulfur. In this process the presence of hydrocarbons, in particular aromatic hydrocarbons such as benzene, toluene or xylene, is harmful, since they impair the quality of the resultant sulfur or damage the catalysts used in SRUs.

Flue gases generally comprise considerable amounts of oxygen. In the removal of carbon dioxide using aqueous amine solutions, the oxygen can dissolve physically to a certain extent in the absorption medium. The dissolved oxygen can, in particular under the conditions of elevated temperature in absorption medium regeneration, lead to a gradual destruction of amines. To avoid this problem it has already been proposed to add stabilizers against oxygen-induced decomposition to the absorption medium. Although the use of stabilizers effectively suppresses decomposition of amines, their use is associated with considerable costs, since the amount of stabilizer must be continually replenished. Since amine decomposition is predominantly caused by the oxygen physically dissolved in the absorption medium, it would be desirable to suppress oxygen coabsorption in the absorption medium.

The object of the invention is to specify a process and an absorption medium for removing acid gases from hydrocarbonaceous or oxygen-comprising fluid streams which indicates reduced coabsorption of hydrocarbons or oxygen without (i) significantly impairing the absorption rate at which acid gases are absorbed; (ii) without significantly reducing the absorption capacity of the solution for acid gases and (iii) without significantly increasing the energy requirement needed for regeneration.

It has now been found that by conjoint use of metal salts of an aminocarboxylic acid and/or aminosulfonic acid in the aqueous solution, the coabsorption of hydrocarbons or oxygen can be reduced without harmful consequences on absorption capacity, absorption rate and energy requirement.

The use of amino acid salts in absorption media is known per se. GB 1 543 748 describes a process for removing $CO_2$ and $H_2S$ from a cracked gas using an aqueous solution of an alkali metal salt of a N-dialkyl-α-aminomonocarboxylic acid, such as dimethylglycine.

U.S. Pat. No. 4,094,957 discloses the removal of $CO_2$ from gas streams using an absorption solution which comprises a basic alkali metal salt, a sterically hindered amine and an amino acid such as N,N-dimethylglycine.

EP-A 671 200 the removal of CO2 from combustion gases of atmospheric pressure using an aqueous solution of an amino acid metal salt and piperazine.

This prior art does not imply the use of an aqueous amine solution which comprises a metal salt of an aminocarboxylic acid and/or aminosulfonic acid for removing acid gases from hydrocarbonaceous or oxygen-comprising fluid streams.

BRIEF SUMMARY

The invention relates to a process for removing acid gases from a hydrocarbonaceous fluid stream or an oxygen-comprising fluid stream in which the fluid stream is contacted with an aqueous solution which is essentially free from inorganic basic salts and comprises (i) at least one amine and (ii) at least one metal salt of an aminocarboxylic acid and/or an aminosulfonic acid.

DETAILED DESCRIPTION

Figure 1:
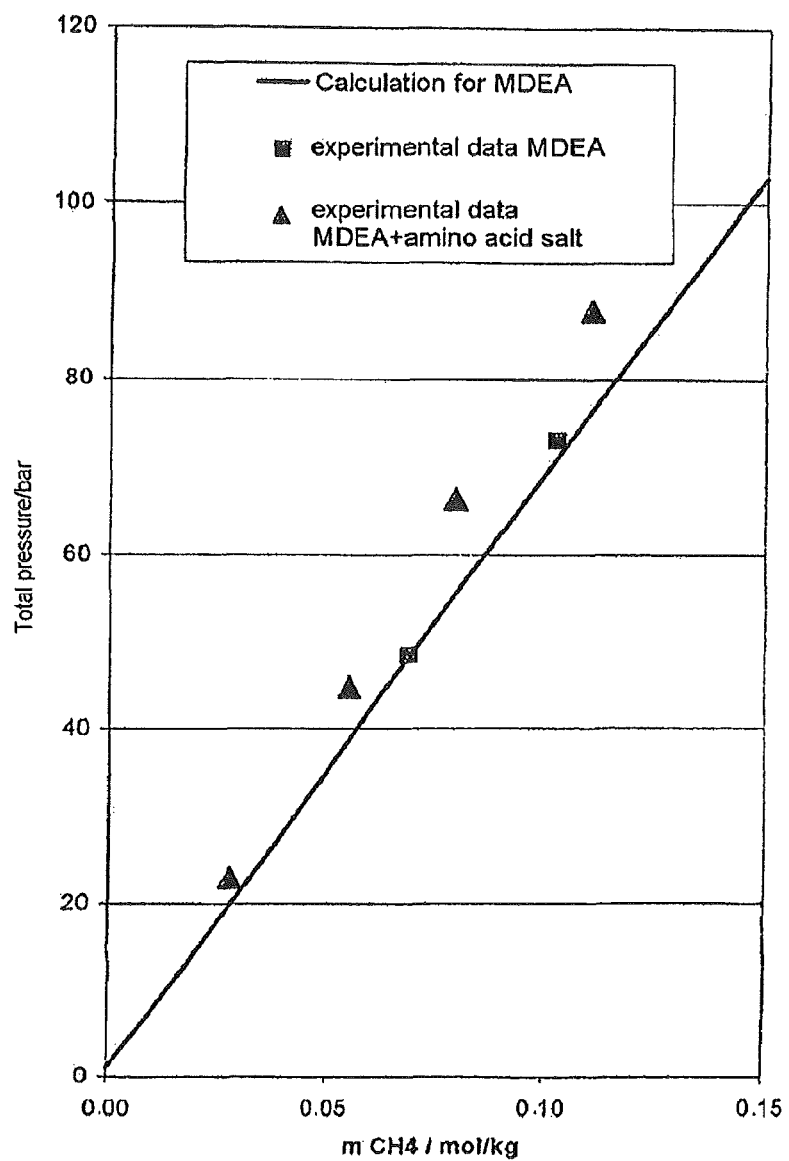
FIG. 1 shows the solubility of methane as a function of pressure in an absorption medium of the invention and in a comparative solvent without amino acid salt.

The invention in addition relates to an absorption medium for removing acid gases from a fluid stream which comprises an aqueous solution which is essentially free from inorganic basic salts and comprises (i) at least one alkanolamine and (ii) a metal salt of an aminocarboxylic acid and/or aminosulfonic acid.

The following details with respect to the process according to the invention apply correspondingly to the absorption medium of the invention and vice versa, provided that it does not appear otherwise from the context.

The metal salt of the aminocarboxylic acid and/or aminosulfonic acid is compatible in the aqueous solution with the amine, in particular the alkanolamine, and does not lead to solubility or storability problems. Its co-use reduces the coabsorption of hydrocarbons or oxygen without significantly impairing the absorption rate at which the acid gases are absorbed; without significantly reducing the absorption capacity of the solution for acid gases and without significantly increasing the energy requirement needed for regeneration.

The aqueous solution is essentially free from inorganic basic salts, that is it preferably comprises less than about 10% by weight, in particular less than about 5% by weight, inorganic basic salts. Inorganic basic salts are, for example, alkali metal or alkaline earth metal carbonates or hydrogencarbonates, such as in particular potassium carbonate (potash). Of course, the metal salt of the aminocarboxylic acid and/or aminosulfonic acid can be obtained by in situ neutralization of an aminocarboxylic acid and/or aminosulfonic acid using an inorganic base such as potassium hydroxide. For this purpose an amount of base significantly going beyond the amount necessary for neutralization is not used in this context.

Aminocarboxylic acids comprise at least one amino group and at least one carboxyl group in their molecular structure. Correspondingly, aminosulfonic acids comprise at least one amino group and at least one sulfonic acid group in their molecular structure.

Suitable aminocarboxylic acids are, for example, α-amino acids, such as glycine (aminoacetic acid), N-methylglycine (N-methylamino acetic acid, sarcosine), N,N-dimethylglycine (dimethylaminoacetic acid), N-ethylglycine, N,N-diethylglycine, alanine (2-aminopropionic acid), N-methylalanine (2-(methylamino)propionic acid), N,N-dimethylalanine, N-ethylalanine, 2-methylalanine (2-aminoisobutyric acid), leucine (2-amino-4-methylpentan-1-acid), N-methylleucine, N,N-dimethylleucine, isoleucine (1-amino-2-methylpentanoic acid), N-methylisoleucine, N,N-dimethylisoleucine, valine (2-aminoisovaleric acid), α-methylvaline (2-amino-2-methylisovaleric acid), N-methylvaline (2-methylaminoisovaleric acid), N,N-dimethylvaline, proline (pyrrolidine-2-carboxylic acid), N-methylproline, serine (2-amino-3-hydroxy-propane-1-acid), N-methylserine, N,N-dimethylserine, 2-(methylamino) isobutyric acid, piperidine-2 carboxylic acid, N-methylpiperidine-2-carboxylic acid.

β-amino acids, such as 3-aminopropionic acid (β-alanine), 3-methylaminopropionic acid, 3-dimethylaminopropionic acid, iminodipropionic acid, N-methyliminodipropionic acid, piperidine-3 carboxylic acid, N-methylpiperidine-3-carboxylic acid, or aminocarboxylic acids such as piperidine-4 carboxylic acid, N-methylpiperidine-4-carboxylic acid, 4-aminobutyric acid, 4-methylaminobutyric acid, 4-dimethylaminobutyric acid.

Suitable aminosulfonic acids are, for example aminomethanesulfonic acid, taurine (2-aminoethanesulfonic acid), N-methyltaurine.

When the aminocarboxylic acid or aminosulfonic acid has one or more chiral carbon atoms, the configuration is of no account; use can be made not only of the pure enantiomers/diastereomers, but also any desired mixtures or racemates.

The aminocarboxylic acid is preferably an α-amino acid or a β-amino acid. The aminosulfonic acid is preferably an α-aminosulfonic acid or a β-aminosulfonic acid. Of these, particular preference is given to α-amino acid and β-aminosulfonic acid. The designation "α" and "β" means, in agreement with the usual nomenclature, that the amino group is separated by one or two, respectively, carbon atoms from the carboxyl group or sulfonic acid group.

Particularly suitable compounds are N-mono-$C_1$-$C_4$-alkylaminocarboxylic acids and N,N-di-$C_1$-$C_4$-alkylaminocarboxylic acids, in particular N-mono-$C_1$-$C_4$-alkyl-α-aminocarboxylic acids and N,N-di-$C_1$-$C_4$ alkyl-α-aminocarboxylic acids.

The metal salt is generally an alkali metal salt or alkaline earth metal salt, preferably an alkali metal salt such as a sodium or potassium salt, of which potassium salts are most preferred.

Particularly preferred metal salts of aminocarboxylic acids are the potassium salt of dimethylglycine or N methylalanine.

Generally, the aqueous solution comprises 2 to 5 kmol/$m^3$, in particular 3.5 to 4.5 kmol/$m^3$ of amine (solely the metal salt of the aminocarboxylic acid and/or aminosulfonic acid) and 0.5 to 2 kmol/$m^3$, in particular 0.7 to 1.5 kmol/$m^3$, of metal salt of the aminocarboxylic acid and/or aminosulfonic acid.

Suitable amines are primary, secondary or tertiary alkylamines and/or alkanolamines. Alkanolamines comprise at least one nitrogen atom which is substituted by at least one hydroxyalkyl group, in particular one $C_2$-$C_3$-hydroxyaklyl group, usually a 2-hydroxyethyl, 2-hydroxypropyl or 3-hydroxypropyl group.

Preferably, the aqueous solution comprises at least one alkanolamine. Suitable alkanolamines are selected from monoethanolamine (MEA), diethanolamine (DEA), diisopropanolamine, triethanolamine (TEA), diethylethanolamine (DEEA), ethyldiethanolamine, aminoethoxyethanol (AEE), dimethylaminopropanol (DIMAP) and methyldiethanolamine (MDEA), methyldiisopropanolamine (MDIPA), 2-amino-2-methyl-1-propanol (AMP), 2-amino-1-butanol (2-AB) or mixtures thereof.

In preferred embodiments, the alkanolamine is a tertiary alkanolamine. In addition, the aqueous solution can comprise one or more activators which are selected from primary and secondary amines. Activators are preferably used when the $CO_2$ uptake is intended to be accelerated by intermediate formation of a carbamate structure.

The tertiary alkanolamine can be a trialkanolamine, alkyldialkanolamine or dialkylalkanolamine. The alkyl groups can be straight chain or branched and generally have one to four carbon atoms. The alkanol groups generally have two to four carbon atoms. Examples of tertiary alkanolamines are: triethanolamine (TEA), tributanolamine, methyldiethanolamine (MOEA), diethylethanolamine (OEEA), dimethylethanolamine, dimethylpropanolamine, methyldiisopropanolamine (MDIPA) and preferably methyldiethanolamine (MDEA).

The activator is preferably selected from
a) 5- or 6-member saturated heterocycles having at least one NH group in the ring, which can comprise one or two further heteroatoms in the ring selected from nitrogen and oxygen, or
b) compounds of the formula $R^1$—NH—$R^2$—$NH_2$, where $R^1$ is $C_1$-$C_6$-alkyl and $R^2$ is $C_2$-$C_6$-alkylene.

Examples of preferred activators are: piperazine, 2-methylpiperazine, N-methyl-piperazine, homopiperazine, piperidine and morpholine, and also 3-methylaminopropylamine.

Further suitable activators are diethylenetriamine, triethylenetetramine, tetraethylenepentamine; 2,2-dimethyl-1,3-diaminopropane, hexamethylenediamine, 1,4-diaminobutane, 3,3-iminotrispropylamine, tris(2-aminoethyl)amine, N-(2-aminoethyl)piperazine, 2-(ethylamino) ethanol, 2-(methylamino)ethanol, 2-(n-butylamino)ethanol, 2-amino-1-butanol (2-AB), aminoethoxyethanol, N-(2-hydroxyethyl)ethylenediamine and N,N'-bis(2-hydroxyethyl) ethylenediamine.

Particularly preferred combinations of tertiary alkanolamines and activators are the following:
(i) methyldiethanolamine and piperazine,
(ii) methyldiethanolamine and methylaminopropylamine,
(iii) methyldiethanolamine and aminoethoxyethanol, or
(iv) methyldiethanolamine and 2-amino-1-butanol.

The absorption medium can also comprise additives such as corrosion inhibitors, enzymes etc. Generally, the amount of such additives is in the range of about 0.01-3% by weight of the absorption medium.

The method and absorption medium according to the invention are suitable for treating fluids, in particular gas streams of all types. The acid gases are in particular $CO_2$, $H_2S$, COS and mercaptans. In addition, $SO_3$, $SO_2$, $CS_2$ and HCN can also be removed. Fluids which comprise the acid gases are firstly gases such as natural gas, synthesis gas, coke oven gas, cracking gas, coal gasification gas, recycle gas, landfill gas and combustion gases, and secondly liquids which are essentially immiscible with the absorption medium, such as LPG (liquefied petroleum gas) or NGL (natural gas liquids). The process and absorption medium of the invention are particularly suitable for treating hydrocarbonaceous fluid streams. The hydrocarbons present are, for example, aliphatic hydrocarbons such as $C_1$-$C_4$ hydrocarbons, such as methane, unsaturated hydrocarbons such as ethylene or propylene, or aromatic hydrocarbons such as benzene, toluene or xylene. The process and absorption medium of the invention are particularly suitable for removing $CO_2$ and $H_2S$.

The oxygen-comprising fluid stream is generally a gas stream which is formed in the following manner:
a) oxidation of organic substances, for example combustion gases or flue gases,
b) composting and storage of waste materials comprising organic substances, or
c) bacterial decomposition of organic substances.

Oxidation can be carried out with appearance of flames, that is as conventional combustion, or as oxidation without appearance of flames, for example in the form of catalytic oxidation or partial oxidation. Organic substances which are subject to combustion are usually fossil fuels such as coal, natural gas, petroleum, gasoline, diesel, raffinates or kerosene, biodiesel or waste materials having a content of organic substances. Starting materials of catalytic (partial) oxidation are, for example, methanol or methane which can be reacted to form formic acid or formaldehyde.

Waste materials which are subject to oxidation, composting or storage, are typically domestic refuse, plastic wastes or packaging refuse.

Combustion of organic substances is usually performed in customary incineration plants with air. Composting and storage of waste materials comprising organic substances generally proceeds on refuse landfills. The exhaust gas or exhaust air of such plants can advantageously be treated by the method of the invention.

As organic substances for bacterial decomposition, customarily use is made of stable manure, straw, liquid manure, sewage sludge, fermentation residues and the like. Bacterial decomposition proceeds, for example, in customary biogas plants. The exhaust air of such plants can advantageously be treated by the method according to the invention.

The starting gas (raw gas) rich in acid gas constituents is contacted with the absorption medium in an absorption step in an absorber, as a result of which the acid gas components are at least in part scrubbed out.

The absorber used is preferably a scrubbing device used in conventional gas scrubbing processes. Suitable scrubbing devices are, for example, dumped packings, arranged packing and tray columns, membrane contacters, radial stream scrubbers, jet scrubbers, Venturi scrubbers and rotary spray scrubbers, preferably arranged packing columns, dumped packing columns and tray columns, particularly preferably tray columns and dumped packing columns. The fluid stream is treated with the absorption medium preferably in a column in countercurrent flow. The fluid is generally introduced into the lower region of the column and the absorption medium into the upper region of the column. In tray columns, sieve trays, bubble-cap trays or valve trays are built in, over which the liquid flows. Dumped packing columns can be packed with various shaped bodies. Heat exchange and mass transfer are improved owing to the increase in surface area as a result of the shaped bodies which are generally about 25 to 80 mm in size. Known examples are the Raschig ring (a hollow cylinder), pall ring, Hiffow ring, Intalox saddles and the like. The dumped packings can be introduced into the column in an ordered manner, or else in a non-ordered manner (as packed bed). Materials which come into consideration are glass, ceramic, metal and plastics. Structured packings are a further development of ordered dumped packings. They exhibit a regular structure. As a result, in the case of arranged packings, it is possible to reduce pressure drops in the gas flow. There are various designs of arranged packings, for example fabric or metal sheet packings. As material, use can be made of metal, plastic, glass and ceramic.

The temperature of the absorption medium in the absorption step is generally about 30 to 100° C., when a column is used, for example 30 to 70° C. at the top of the column and 50 to 100° C. at the bottom of the column. The overall pressure in the absorption step is generally about 1 to 120 bar, preferably about 10 to 100 bar.

A product gas (clean gas) which is low in acid gas components, that is to say depleted in these components, is obtained, and an absorption medium loaded with acid gas components is obtained. The process of the invention can comprise one or more, in particular two, sequential absorption steps. The absorption can be carried out in a plurality of sequential substeps, the raw gas comprising the acid gas components being contacted in each of the substeps with in each case a substream of the absorption medium. The absorption medium with which the raw gas comes into contact can already be in part loaded with acid gases, that is to say it can be an absorption medium which has been recirculated from a subsequent absorption step to the first absorption step, or a partially regenerated absorption medium. With respect to carrying out the two-stage absorption, reference is made to the publications EP-A 0 159 495, EP-A 0 20 190434, EP-A 0 359 991 and WO 00100271.

According to a preferred embodiment, the process of the invention is carried out in such a manner that the fluid comprising the acid gases is first treated with the absorption medium in a first absorption step at a temperature of 40 to 100° C., preferably 50 to 90° C., and in particular 60 to 90° C. The fluid depleted in acid gases is then treated with the absorption medium in a second absorption step at a temperature of 30 to 90° C., preferably 40 to 80° C., and in particular 50 to 80° C. The temperature in this step is 5 to 20° C. lower than in the first absorption step.

The acid gas components can be released from the absorption medium loaded with the acid gas components in a conventional manner (similarly to the publications cited hereinafter) in a regeneration step, a regenerated absorption medium being obtained. In the regeneration step, the loading of the absorption medium is reduced and the resultant regenerated absorption medium is preferably subsequently recirculated to the absorption step.

Generally, the regeneration step comprises at least one pressure relaxation of the loaded absorption medium from a high pressure, as prevails when the absorption step is carried out, to a lower pressure. The pressure expansion can be achieved, for example, by means of a throttle valve and/or an expansion turbine. Regeneration using an expansion stage is described, for example, in the publications U.S. Pat. No. 4,537,753 and U.S. Pat. No. 4,553,984.

The acid gas components can be released in the regeneration step, for example in an expansion column, for example a vertical or horizontal flash vessel, or a countercurrent flow column having internals.

The regeneration column can if appropriate be a dumped packing column, arranged packing column or tray column. The regeneration column at the bottom has a reboiler, for example a forced circulation evaporator with circulation pump. At the top the regeneration column has an outlet for the released acid gases. Entrained absorption medium vapors are condensed in a condenser and recirculated to the column.

A plurality of expansion columns can be connected in series, in which regeneration is performed at different pressures. For example, regeneration can be performed in a preliminary expansion column at high pressure which is typically about 1.5 bar above the partial pressure of the acid gas components in the absorption step, and in a main expansion column at low pressure, for example 1 to 2 bar absolute. Regeneration using two or more expansion stages is described in the publications U.S. Pat. No. 4,537,753, U.S. Pat. No. 4,553,984, EP-A 0 159 495, EP-A 0 202 600, EP-A 0 190 434 and EP-A 0 121 109.

DE 100 28 637 describes a process variant having two low pressure expansion stages (1 to 2 bar absolute) in which the absorption liquid which is partially regenerated in the first low pressure expansion stage is warmed, and in which if appropriate upstream of the first low pressure expansion stage a medium pressure expansion stage is provided in which expansion is performed to at least 3 bar. In this process, the loaded absorption liquid is first expanded to a pressure of 1 to 2 bar (absolute) in a first low-pressure expansion stage. Subsequently, the partially regenerated absorption liquid is warmed in a heat exchanger and then again expanded to a pressure of 1 to 2 bar (absolute) in a second low-pressure expansion stage.

The last expansion stage can also be carried out under vacuum which is generated, for example, by means of a steam jet pump, if appropriate in combination with a mechanical vacuum generation device as described in EP-A 0 159 495, EP-A 0 202 600, EP-A 0 190 434 and EP-A 0 121 109 (U.S. Pat. No. 4,551,158).

Because of optimum matching of the content of amine components, the absorption medium of the invention has a high loading capacity with acid gases which can also be readily desorbed again. As a result, in the process of the invention, the energy consumption and the solvent circulation can be significantly reduced.

The invention will be described in more detail on the basis of the accompanying drawing and the examples hereinafter.

FIG. 1 shows the solubility of methane as a function of pressure in an absorption medium of the invention and in a comparative solvent without amino acid salt.

Figure 2:
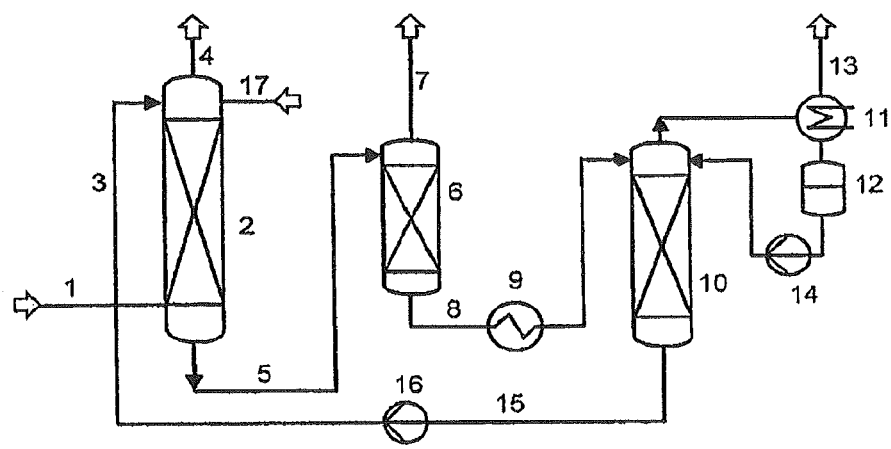
FIG. 2 shows diagrammatically a device suitable for carrying out the process according to the invention.
Figure 3:
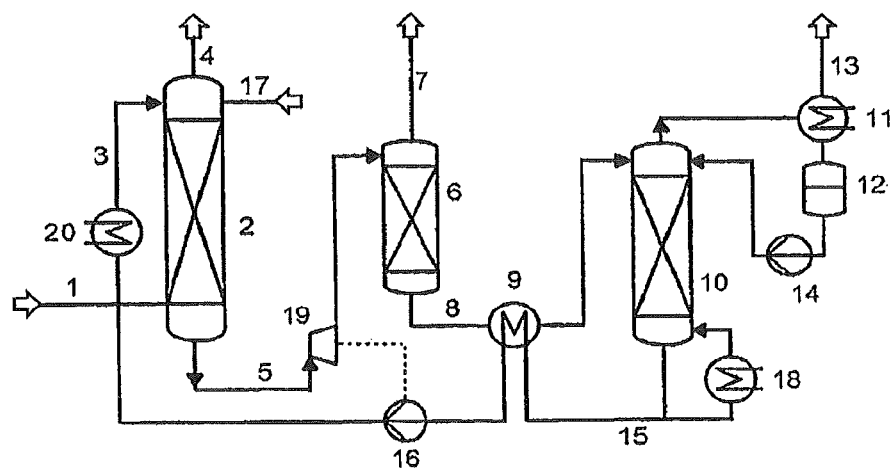
FIG. 3 shows diagrammatically a device suitable for carrying out the process according to the invention.

FIGS. 2 and 3 show diagrammatically a device suitable for carrying out the process according to the invention.

FIG. 2 diagrammatically illustrates a device in which the absorption stage is carried out as a single stage and the expansion stage as two stages. The feed gas is fed in via line 1 to the lower region of the absorber 2. The absorber 2 is a column which is packed with dumped packings in order to achieve the mass transfer and heat exchange. The absorbent which is regenerated absorbent having a low residual content of acid gases is applied via line 3 to the top of the absorber 2 in countercurrent flow to the feed gas. The gas depleted in acid gases leaves the absorber 2 overhead (line 4). The absorbent enriched with acid gases leaves the absorber 2 at the bottom via line 5 and is introduced into the upper region of the high-pressure expansion column 6, which is generally operated at a pressure which is above the acid gas partial pressure of the raw gas fed to the absorber. The absorption medium is generally expanded using conventional devices, for example a level control valve, a hydraulic turbine or a pump running in reverse. In the expansion, the majority of the dissolved non-acid gases and also a small part of the acid gases are released. These gases are ejected from the high-pressure expansion column 6 overhead via line 7.

The absorption medium which is still loaded with the majority of the acid gases leaves the high-pressure expansion column via line 8 and is heated in heat exchanger 9, in which a small part of the acid gases can be released.

The heated absorption medium is introduced into the upper region of a low-pressure expansion column 10 which is equipped with a dumped-packing packed bed in order to achieve a high surface area and thus to cause the release of the acid gases and establish equilibrium. In the low-pressure expansion column 10, the majority of the acid gases is virtually completely released by flashing. The absorption medium is in this manner simultaneously regenerated and cooled. At the top of the low-pressure expansion column 10, a reflux cooler 11 having a collection vessel 12 is provided in order to cool the released acid gases and to condense a part of the vapor. The majority of the acid gas leaves the reflux cooler 11 via line 13. The condensate is pumped back by means of pump 14 to the top of the low-pressure expansion column 10. The regenerated absorption medium which still contains a small part of the acid gases leaves the low-pressure expansion column 10 at the bottom via line 15 and is applied by means of pumps 16 via line 3 to the top of the absorber 2. Via line 17, fresh water can be fed in to make up for the water discharged with the gases.

FIG. 3 shows diagrammatically a device for carrying out the process of the invention having an expansion stage and a desorption stage (stripper).

The feed gas is fed in via line 1 to the lower region of the absorber 2. The absorption medium is applied via line 3 to the top of the absorber 2 in countercurrent flow to the feed gas. The gas which is depleted in acid gases leaves the absorber 2 overhead (line 4). The absorption medium which is enriched with acid gases leaves the absorber 2 at the bottom via line 5 and is introduced via an expansion turbine 19 to the upper region of the high-pressure expansion column 6, which is generally operated at a pressure which is above the $CO_2$ partial pressure of the raw gas fed to the absorber. In the expansion, the majority of the dissolved non-acid gases and also a small part of the acid gases are released. These gases are ejected from the high-pressure expansion column 6 overhead via line 7. The energy arising at the expansion turbine 19 can be used for operating the pump 16.

The absorption medium which is still loaded with the majority of the acid gases leaves the high-pressure expansion column via line 8 and is heated in the heat exchanger 9 by indirect heat exchange with regenerated absorption medium which is passed in via line 15.

The heated loaded absorption medium is introduced into the upper region of a desorber column 10. The column 10 has indirect bottom heating via the heat exchanger 18. In the column 10, a part of the $CO_2$ and $H_2S$ is released by flashing, the remainder is expelled virtually completely by stripping in the lower part of the column 10. At the top of the column 10, a reflux cooler 11 having a collection vessel 12 is provided, in order to cool the released acid gases and to condense a part of the vapor. The majority of the acid gas leaves the reflux cooler 11 via line 13. The condensate is pumped back to the top of the column 10 by means of pump 14. The regenerated absorption medium leaves the column 10 at the bottom via line 15 and, via heat exchanger 9, is applied to the top of the absorber 2 by means of pump 16 via line 3 and the cooler 20. Via line 17, fresh water can be fed in to make up for the water discharged with the gases.

EXAMPLE

Use was made of an absorption medium of the following composition: 40% by weight methyldiethanolamine and 60% by weight of water. This absorption medium served as comparative absorption medium.

An absorption medium of the invention was obtained by admixing the comparative absorption medium with 10% by weight of potassium salt of dimethylglycine.

Both absorption media were preloaded with 20 $Nm^3$ of carbon dioxide/t absorption medium. The solubility of methane in both absorption media was then determined at various methane partial pressures by. The results are shown in FIG. 1.

It may be seen that in the absorption medium of the invention, at the same methane partial pressure, significantly less methane is soluble. It is expected that the reduction of solubility is still more pronounced in the case of longer-chain and unsaturated hydrocarbons than in the case of methane.

The invention claimed is:

1. A process for removing acid gases from a hydrocarbonaceous fluid stream which comprises
   contacting the fluid stream with an aqueous solution which is essentially free from inorganic basic salts and comprises
   (i) 2 to 5 $kmol/m^3$ of methyldiethanolamine, and
   (ii) 0.5 to 2 $kmol/m^3$ of at least one metal salt of an aminocarboxylic acid, at least one metal salt of an aminosulfonic acid, or a mixture of at least one metal salt of an aminocarboxylic acid and at least one metal salt of an aminosulfonic acid,
   wherein the overall pressure while contacting the fluid stream with aqueous solution is 10 to 100 bar.

2. The process according to claim 1, wherein the aminocarboxylic acid is an α-amino acid or a β-amino acid and the aminosulfonic acid is an α-aminosulfonic acid or a β-aminosulfonic acid.

3. The process according to claim 1, in which the metal salt is an alkali metal or alkaline earth metal salt.

4. The process according to claim 1, wherein the metal salt of the aminocarboxylic acid is the potassium salt of N,N-dimethylglycine or N-methylalanine.

5. The process according to claim 1, wherein component (ii) is 0.5 to 2 $kmol/m^3$ of at least one metal salt of an aminosulfonic acid.

6. The process according to claim 1, wherein component (ii) is 0.5 to 2 $kmol/m^3$ of a mixture of at least one metal salt of an amino carboxylic acid and at least one metal salt of an aminosulfonic acid.

7. The process according to claim 1, wherein the aminocarboxylic acid is a N-mono-$C_1$-$C_4$-alkylaminocarboxylic acid or a N,N-di-$C_1$-$C_4$-alkylaminocarboxylic acid.

8. The process according to claim 7, wherein the metal salt of the aminocarboxylic acid is the potassium salt of N,N-dimethylglycine or N-methylalanine.

9. The process according to claim 1, in which the aqueous solution in addition comprises one or more activators.

10. The process according to claim 9, wherein the activator is selected from the group consisting of piperazine, methylaminopropylamine, aminoethoxyethanol and 2-amino-1-butanol.

11. The process according to claim 10, wherein the aqueous solution comprises methyldiethanolamine and piperazine.

12. The process according to claim 10, wherein the aqueous solution comprises:
    (i) methyldiethanolamine and methylaminopropylamine,
    (ii) methyldiethanolamine and aminoethoxyethanol, or
    (iii) methyldiethanolamine and 2-amino-1-butanol.

* * * * *